United States Patent [19]

Kao et al.

[11] 4,374,256
[45] Feb. 15, 1983

[54] PROCESS FOR THE PREPARATION OF PYRRYL-2-ACETONITRILE

[75] Inventors: James T. F. Kao; Karl E. Wiegand, both of Baton Rouge, La.

[73] Assignee: Ethyl Corporation, Richmond, Va.

[21] Appl. No.: 8,943

[22] Filed: Feb. 2, 1979

Related U.S. Application Data

[63] Continuation of Ser. No. 582,860, Jun. 2, 1975, abandoned.

[51] Int. Cl.³ .................................... C07D 207/337
[52] U.S. Cl. .................................................. 548/561
[58] Field of Search ................................ 260/376.62

[56]  References Cited

U.S. PATENT DOCUMENTS 3,523,952  8/1970  Orth et al. .............. 260/326.62
3,882,146  5/1975  Wiegand .................. 260/326.62

OTHER PUBLICATIONS

Whitmore; Org. Chem., vol. 1, pp. 72-82, 165, 166, 167, (1951).
Carson et al.; J. Org. Chem., vol. 42, pp. 1096-1097, (1977).

*Primary Examiner*—Mary C. Lee
*Attorney, Agent, or Firm*—Donald L. Johnson; John F. Sieberth; James M. Pelton

[57] ABSTRACT

Pyrryl-2-acetonitriles corresponding to the formula

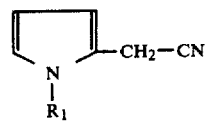

in which $R_1$ stands for hydrogen or an alkyl group having 1-4 carbon atoms prepared from dialkyl-(pyrryl-2-methyl)-amine corresponding to the formula

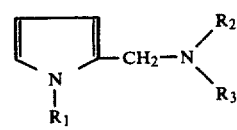

in which $R_1$ is defined as above and $R_2$ and $R_3$ stand for alkyl groups having 1-4 carbon atoms, are alkylated with alkyl halides such as methyl chloride or methyl bromide to form the corresponding trialkyl-(pyrryl-2-methyl)-ammonium chloride quaternary salts and then reacted with an aqueous solution of alkali cyanide in the presence of a water-immiscible solvent under conditions which provide more economical utilization of reactants and process equipment.

6 Claims, No Drawings

PROCESS FOR THE PREPARATION OF PYRRYL-2-ACETONITRILE

CROSS REFERENCE TO RELATED APPLICATION

This application is a continuation of application Ser. No. 582,860, filed June 2, 1975, now abandoned.

BACKGROUND OF THE INVENTION

It has been known to prepare pyrryl-2-acetonitriles, for example, pyrryl-2-acetonitrile and N-methylpyrryl-2-acetonitrile, by reacting trimethyl-(pyrryl-2-methyl)-ammonium-iodide or trimethyl-(N-methylpyrryl-2-methyl)-ammonium-iodide, respectively, with sodium cyanide. Trimethyl-(pyrryl-2-methyl)-ammonium-iodide and trimethyl-(N-methylpyrryl-2-methyl)-ammonium-iodide are formed in known manner by adding methyl iodide to an alcoholic solution of dimethyl-(pyrryl-2-methyl)-amine or dimethyl-(N-methylpyrryl-2-methyl)-amine, respectively, see *J. Amer. Chem. Soc.* 73, 4921 (1951) and *J. Amer. Chem. Soc.* 75, 483 (1953).

The above mentioned processes have particularly the disadvantage that the ammonium salts prepared from the Mannich bases by reaction with alkyl iodides in absolute alcohol must be isolated prior to their further reaction to the corresponding nitriles. Furthermore, the isolated ammonium compounds decompose easily, whereby the yield of pyrrylacetonitriles is adversely affected.

To overcome the above difficulties, Orth et al. in U.S. Pat. No. 3,523,952 conducted the displacement in a water-immiscible solvent. On the scale disclosed in the examples, the procedure of Orth et al apparently is satisfactory since the addition of the alkali cyanide to the quaternary salt at room temperature does not produce reaction. However, upon heating the reaction mixture to 80° C., the reaction starts and is completed by maintaining the temperature for two hours. Since the reaction is exothermic, such procedures are not practical for large scale operations because the exotherm causes severe evolution of gas, foaming and is difficultly controlled upon heating the entire reaction mass. The process of the present invention has been found to overcome these disadvantages. There is provided an extremely efficacious and practical process for the production of pyrryl-2-acetonitriles.

THE INVENTION

The present invention provides improvement in a process for the preparation of pyrryl-2-acetonitriles corresponding to the formula

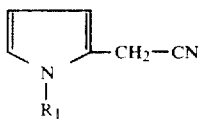

wherein $R_1$ is hydrogen or an alkyl group having 1-4 carbon atoms, by reacting a dialkyl-(pyrryl-2-methyl)-amine corresponding to the formula

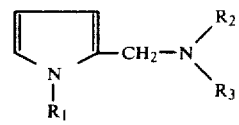

wherein $R_1$ is hydrogen or an alkyl group having 1-4 carbon atoms and $R_2$ and $R_3$ are independently selected from alkyl groups having 1-4 carbon atoms with an alkylating agent selected from an alkyl halide to produce the corresponding trialkyl-(pyrryl-2-methyl)-ammonium halide salt and reaction of said salt with aqueous alkali metal cyanide in the presence of a water-immiscible solvent in which the pyrryl-2-acetonitrile is soluble, the improvement comprising carrying out the quaternization reaction with an alkyl halide having up to 2 carbon atoms and a boiling point not greater than about 20° C. at atmospheric pressure and at a pressure not greater than about 500 psig and carrying out the displacement reaction using from about 110 to about 150 percent by weight of the stoichiometric amount of said alkali metal cyanide based on said dialkyl-(pyrryl-2-methyl)-amine at a temperature of from about 75° to about 100° C., said solvent being present in an amount of from about 1.5 to about 10 parts per part of said dialkyl-(pyrryl-2-methyl)-amine.

In general, the process of the present invention contemplates two reaction stages, quaternization and displacement. Many of the reactants employed can be similar to those used in U.S. Pat. No. 3,523,952 which is hereby incorporated by reference as if fully set forth. Of course the process by which the reactants are employed will vary from the procedure outlined in the U.S. Pat. No. 3,523,952 as further discussed hereinbelow.

As mentioned in U.S. Pat. No. 3,523,952, the process involves treating a Mannich base, such as a dialkyl-(pyrryl-2-methyl)-amine, with an alkyl halide alkylating agent under conditions to facilitate the quaternization reaction and obtain substantially quantitative yields of the corresponding quaternary salt. In the displacement step, the quaternary salt formed is then treated with an alkali cyanide whereby the amine is displaced by the cyanide forming the desired pyrryl-2-acetonitrile. According to the present invention, the process of the displacement reaction is conducted by controlling the rate of feed of the quaternary salt to the hot aqueous alkali cyanide in the presence of the water-immiscible solvent so that the evolution of gas during the displacement is controlled and gradual and accomplished without excessive foaming, rapid increase in pressure or temperature from the reaction which is exothermic in nature. Also, the controlled feed in the displacement reaction allows substantial decrease in the amount of alkali cyanide employed without decreasing the yield of the desired pyrryl-2-acetonitrile. Such advantages can be obtained in the process of this invention using an alkyl halide alkylating agent. Particularly an alkyl halide having a boiling point not greater than about 20° C. at atmospheric pressure can be employed in the process of this invention. Preferably, such alkyl halides having up to 2 carbon atoms are found to be suitable. More preferably, such alkyl halide in which the halogen is chlorine or bromine can be advantageously used in the present process. For example, methyl chloride, methyl bromide, ethyl chloride and similar alkyl halides can be used, with methyl chloride being preferred. The displacement reaction can be carried out by either feeding the quaternary salt to the aqueous alkali cyanide or the reverse. The above procedures accomplish production of pyrrole-2-acetonitriles with a high ratio of this desired material as compared to other isomers, such as nuclear-substituted cyanides, e.g., 1,2-dimethyl-5-cyanopyrrole.

The amount of alkylating agent employed in the present process can range from the stoichiometric amount to a large excess. It is preferred to employ excess alkyl halide alkylating agent to insure that all of the Mannich base is reacted. Also, more alkylating agent available for reaction decreases substantially the time required for reaction. In general, the amount of alkylating agent employed can be expressed as a percentage of the stoichiometric amount required for reaction with the Mannich base. Typically, the amount of alkyl halide used in the present process can range from 100 to about 200 percent of the stoichiometric amount of alkyl halide based on the Mannich base, i.e., the dialkyl-(pyrryl-2-methyl)-amine. Preferably from about 110 to about 150 percent of the stoichiometric amount of alkyl halide, on the same basis, can be used. Most preferably from 120 to about 130 percent of the stoichiometric amount of alkyl halide can be employed in the present process. The dialkyl groups on the amino radical can be an alkyl group having 1-4 carbon atoms such as methyl, ethyl, propyl or butyl or their isomers, as defined for $R_2$ and $R_3$ hereinabove.

Because of the exothermic nature of the alkylation reaction, the reaction mixture is cooled during the quaternization step. Any suitable means conventional in the art can be employed and is well understood by skilled practitioners in the art. In general, the alkylating agents are normally gaseous under ambient conditions and most of the alkyl halide alkylating agents useful in this invention have limited solubility in aqueous systems. It is therefore advantageous to conduct the quaternization step under pressures greater than atmospheric pressure in order to solubilize the reactants in the aqueous reaction mixture. Without limiting the process of this invention, it is believed that the quaternization reaction occurs in the aqueous phase. Thus, the use of pressures greater than atmospheric facilitates solubilization of the alkyl halide alkylating agent, thus increasing contact of reactants and yield. Pressures from about 20 to about 150 psig can be employed. However, pressures greater than about 150 psig require more expensive pressure reactors and are less desirable from a capital investment viewpoint.

The reaction mixture requires somewhat higher than ambient temperatures to obtain a good rate of reaction. In general, temperatures in the range from about 20° to about 50° C. can be employed in the process. Preferably, temperatures for the quaternization reaction of about 30° to about 40° C. have been found useful. Although somewhat higher temperatures can be used without seriously affecting the reaction, the attendant increase in pressures at such higher temperatures would require more expensive pressure reactors which, as indicated above, would increase capital investment in a commercial operation.

Preferably, the reaction is conducted in aqueous suspension with stirring to insure intimate contact of reactants. The reaction proceeds for a time sufficient to allow the reactants to substantially complete the reaction. The alkylating agent can be added to the reactor over a period of from about 0.5 to about 3 hours or more based on the amount of alkylating agent used and the scale of the operation. After the addition of the alkylating agent, the reaction mixture can be held with stirring to assure completion of the reaction. It is convenient to maintain the reaction mixture for a period of from 1 to about 2 or more hours, again depending on the scale of operation. Completion of the reaction can be checked by analysis of the reaction mixture for unreacted Mannich base, e.g., dialkyl-(pyrryl-2-methyl)-amine. For convenience, if the reaction contains one phase then it can be assumed that the reaction was complete.

The displacement step is carried out by the controlled reaction of the quaternary salt with aqueous alkali cyanide solution of water-immiscible solvent. Any suitable alkali cyanide can be employed, such as sodium or potassium cyanide, preferably sodium cyanide. The amount of alkali cyanide should be sufficient to react with the quaternary salt produced. It has been found that an excess of alkali cyanide is required to obtain adequate yields. Previously, over 100 percent excess has been employed. However, it has been found that from about 10 to about 80 percent excess is sufficient to obtain good yields by the process of the present invention. More preferably a 25 to 40 percent excess of alkali cyanide can be used. Stated in other words, the amount of alkali cyanide employed can be within the range of 110 to about 180 weight percent of the stoichiometric amount based on the Mannich base, i.e., the dialkyl-(pyrryl-2-methyl)-amine. Preferably, an amount of alkali metal cyanide of from about 125 to about 140 weight percent of the stoichiometric amount based on the Mannich base, i.e., the dialkyl-(pyrryl-2-methyl)-amine can be used. The order of addition of reactants in the displacement reaction is not critical. Either quaternary salt is added to the alkali metal cyanide or the alkali metal cyanide to the quaternary salt as desired. Whatever order of addition is selected, the feed rate is controlled to prevent the exothermic reaction from becoming uncontrollable. The feed rate should be sufficient to provide adequate yield of the desired pyrryl-2-acetonitriles, but not so low as to require unreasonably long cycle times. Typically, the aqueous phase produced in the quaternization reaction can be fed to the aqueous alkali cyanide solution at the rate of about 3.5 to about 10 parts by weight per minute. Such rates can also be employed in feeding the aqueous alkali cyanide to the aqueous quaternary salt mixture in the presence of the water-immiscible solvent.

The water-immiscible solvent can be any liquid which is substantially inert to the reactants and has sufficient solvent power for dissolving the product pyrryl-2-acetonitriles. Examples of such solvents are benzene and its homologs and halogenated alkanes, such as for example, benzene, toluene, xylene, chlorinated hydrocarbons having a boiling point above the reaction temperature, e.g., ethylene chloride, trichloroethylene, perchloroethylene, methyl chloroform, and the like. Such solvents are conventional and described in U.S. Pat. No. 3,523,952, supra. The amount of solvent employed should be only that amount sufficient to maintain an easily stirred reaction mixture. For convenience, the amount of solvent employed is stated in terms of the amount of starting Mannich base employed. The effect of the amount of solvent being too low is to depress the yield of pyrryl-2-acetonitriles produced. Thus, it is preferred to employ at least about 1.50 parts of solvent per part of Mannich base, i.e., per part of dialkyl-(pyrryl-2-methyl)-amine. Preferably, from about 1.5 to about 10 parts of solvent per part of Mannich base can be used. However, to reduce the size of reaction equipment and increase reactor productivity an intermediate range is preferred. For example, from about 2.75 to about 3.50 parts of solvent per part of Mannich base has been found to give acceptable yields without unduly increasing capital investment or decreasing productivity of a given reaction vessel.

The reaction temperature of the displacement reaction depends somewhat upon the solvent selected and the stage of reaction. The reaction begins about 80° C. and the temperature is controlled, preferably between about 76° to about 85° C. by refluxing. The temperature being initially at the upper portion and gradually decreasing slightly as the low boiling by-product amine forms. Further, it is preferred that the controlled addition of the quaternary salt or the aqueous alkali cyanide, depending on the reactants selected, take place over a time sufficient to allow adequate venting, heat transfer and yield. In general, cycle times of from about 2 to about 8 hours or more, depending upon the scale of operation and the temperature employed, can be used.

In general, the overall procedure with the preparation of the pyrryl-2-acetonitrile compounds of this invention can be described as follows. To a suitable reaction vessel is charged the Mannich base and water. The reactor agitator and heating medium on the reactor are started. Then, the reactor contents are warmed to about 50° C. and the alkyl halide alkylating agent is added until the desired amount is present over a period of about 60–180 minutes sufficient to maintain the reaction temperature at about 40° C. and the pressure at about 50 psig. The alkylating agent feed is stopped and reaction conditions are maintained for a period sufficient to allow completion of the reaction, for example, about 60 to about 120 minutes, after which the reaction mixture is checked to see whether a clear water-soluble, one-phase solution, is obtained. If this is the case, the procedure is continued. If not, agitation is continued unitl a clear water-soluble, one-phase solution is obtained. In a separate reactor, are added toluene and water. The agitator is activated and solid sodium cyanide is added to the reactor. Caution should be observed in adding the sodium cyanide because of its toxicity. The reactor is heated to reflux at about 90° C. The reaction mixture from the first reactor is then added to the second reactor at a rate sufficient to obtain good reaction without foaming or pressure build-up from displacement of alkylamine, for example, about one gallon per minute and reflux is maintained for about 120 minutes after completing the addition. After this period, the phases are allowed to separate and the bottom aqueous phase is removed. The organic phase is transferred to product recovery operations.

In accord with this procedure, the present invention provides an easily controllable reaction procedure with high ratios of the desired pyrryl-2-acetonitrile. The following examples illustrate the invention but should not be considered as limiting thereof.

EXAMPLE 1

To a suitable reactor was added 276 parts of the Mannich base dimethyl-(N-methylpyrryl-2-methyl)-amine and 300 parts of water. The stirrer was activated and heating started on the reaction vessel to bring the reaction mixture to 40° C. Methyl chloride liquid was then added at a controlled rate. The temperature was maintained at 40° C. with a slight cooling during the addition which took 73 minutes. Pressure increased slowly during addition and reached 50 psig at the end of addition. After addition, the stirring was continued for another 87 minutes. A one-phase aqueous solution was obtained.

In another reactor there was mixed 865 parts of toluene and 257 parts of water with stirring. To this was added 128 parts of sodium cyanide, representing about 130% of theory based on the Mannich base. While continuing the stirring, the cyanide solution was heated to reflux, about 88° C. and held at reflux. Then the aqueous solution from the first reactor was added to the refluxing cyanide over a period of about 60 minutes. After completing addition, the reaction mixture continued to reflux for another 120 minutes. During addition and for some time during the continued reflux a gas was evolved and vented which on an analysis was determined to be trimethyl amine. After refluxing was completed, the reaction mixture was cooled to about 40° C. and allowed to stand while the phases separated. The aqueous phase was removed and the organic phase was analyzed by vapor phase chromatograph with the following results:

|   | Mole % |
|---|---|
| 1. Trimethylamine | 0.22 |
| 2. Starting Mannich base | 0.20 |
| 3. Toluene | 73.1 |
| 4. 1,2-Dimethyl-5-cyanopyrrole | 1.4 |
| 5. N—methylpyrrole-2-acetonitrile | 14.9 |
| Total | 89.77 |

The lack of closure on analysis was due to the heavy materials which would not show up in VPC analysis.

Following the sequence of steps outlined above, a series of runs was made changing different variables including reflux temperature, time of addition, amount of alkylating agent and the pressure of alkylating agent in the reactor to determine their effect on the production of pyrryl-2-acetonitriles by the process of the present invention. Table I shows the results of these runs.

As described above, the procedure is carried out in two stages, quaternization of the Mannich base, which for illustration employs dimethyl-(N-methylpyrryl-2-methyl)-amine, and displacement. In the quaternization step equimolar amounts of Mannich base and alkylating agent were usually employed for other types of alkylating agent. However, for methyl chloride, excess can be used without adverse effect. In fact, it helps to push the reaction to completion. Table I uses methyl chloride as the alkylating agent for illustration only. The displacement was run under the same conditions to enable comparison of the quaternization reaction variables.

In Table I, the quaternization step was conducted using temperatures from 23°–43° C., addition times of 30 to 180 minutes, holding times of 60 to 120 minutes, pressures from 31 to 90 psig, and from 100 to 200 percent of the stoichiometric amount of alkylating agent.

TABLE I

PREPARATION OF N—METHYLPYRROLE-2-ACETONITRILE USING METHYL CHLORIDE (MC) AS ALKYLATING AGENT

| Example No. | 2 | 3 | 4 | 5 | 6 |
|---|---|---|---|---|---|
| Quaternization |  |  |  |  |  |
| Mannich Base Purity, % | 100 | 100 | 100 | 100 | 100 |
| % MC Added[1] | 100 | 113 | 127 | 200 | 129 |
| Temp., °C. | 23–43 | 34–40 | 38–40 | 34–40 | 40 |

TABLE I-continued
PREPARATION OF N—METHYLPYRROLE-2-ACETONITRILE USING METHYL CHLORIDE (MC) AS ALKYLATING AGENT

| Example No. | 2 | 3 | 4 | 5 | 6 |
|---|---|---|---|---|---|
| Max. Pressure, psig | 40 | 31 | 43 | 90 | 54 |
| Time, Min.[1] | 180 + 120 | 180 + 60 | 30 + 120 | 130 + 75 | 60 + 120 |
| Cyanide Displacement | | | | | |
| NaCN, % Theory | 130 | 130 | 130 | 130 | 130 |
| Reflux Temp., °C. | 92–82 | 92–84 | 92–84 | 90–82 | 92–82 |
| Time, Min.[2] | 60–120 | 60–120 | 60–120 | 60–120 | 60–120 |
| VPC Result: Mole %[3] | | | | | |
| (1) Mannich Base | 18.0 | 2.5 | 1.5 | — | — |
| (2) 1,2-Dimethyl-5-cyanopyrrole | 3.5 | 6.6 | 4.3 | 5.3 | 5.3 |
| (3) N—methylpyrryl-2-acetonitrile | 52.0 | 60.0 | 58.0 | 65.0 | 63 |
| (4) Ratio of 3:2 | 14.6 | 9.0 | 13.6 | 12.3 | 11.8 |
| (5) Heavy End[4] | 15.4 | 33.4 | 36.2 | 29.7 | 31.7 |

[1]Percent of stoichiometric amount of methyl chloride added based on amount of Mannich base.
[2]Addition + holding.
[3]Based on Mannich base charged.
[4]By difference.

What is claimed is:

1. In a process for the production of pyrryl-2-acetonitriles of the formula

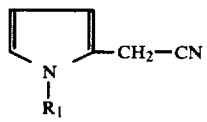

wherein $R_1$ is hydrogen or an alkyl group having 1–4 carbon atoms by reacting a dialkyl-(pyrryl-2-methyl)-amine corresponding to the formula

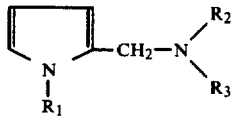

wherein $R_1$ is defined as above and $R_2$ and $R_3$ are independently selected from the same or different alkyl groups having 1 to about 4 carbon atoms with an alkyl halide alkylating agent to form the corresponding quaternary salt and displacing the amine group on said salt with aqueous alkali metal cyanide in the presence of a water-immiscible solvent in which the product pyrryl-2-acetonitrile is soluble, the improvement consisting essentially of alkylating said dialkyl-(pyrryl-2-methyl)-amine with methyl chloride while maintaining a temperature in the range of about 30° to about 40° C. and the pressure at from 20 to about 150 psig to form the corresponding quaternary salt and displacing the amine group from said salt by reaction of about 110 to 180 percent by weight of the stoichiometric amount of said alkali metal cyanide based on said dialkyl-(pyrryl-2-methyl)-amine at a temperature of about 75° to about 100° C. in the presence of from about 1.5 to about 10 parts of said solvent per part of said dialkyl-(pyrryl-2-methyl)-amine, said exothermic displacement reaction being controlled by addition to a mixture of said aqueous alkali metal cyanide and water-immiscible solvent of from about 3.5 to about 10 parts by weight of the quaternary salt aqueous phase per part of said mixture.

2. The process of claim 1 wherein said solvent is present at from about 3 to about 5 parts per part of said dialkyl-(pyrryl-2-methyl)-amine.

3. The process of claim 1 wherein said alkyl halide alkylating agent used is from about 100 to about 200 percent of the stoichiometric amount of said alkyl halide based on the dialkyl-(N-methylpyrryl-2-methyl)-amine.

4. The process of claim 1 wherein said alkyl halide alkylating agent used is from about 110 to about 150 percent of the stoichiometric amount of said methyl chloride based on the dialkyl-(N-methylpyrryl-2-methyl)-amine.

5. The process of claim 1 wherein the quaternization reaction is carried out at a pressure of from about 30 to about 90 psig.

6. The process of claim 1 wherein the quaternization reaction is carried out using about 110 to about 150 percent of the stoichiometric amount of said methyl chloride based on the dialkyl-(N-methylpyrryl-2-methyl)-amine and the pressure is from about 30 to about 90 psig.

* * * * *